United States Patent [19] [11] 3,956,372
Coleman, Jr. et al. [45] May 11, 1976

[54] PROCESS FOR THE PRODUCTION OF PETROLEUM SULFONATE

[75] Inventors: John R. Coleman, Jr., Robinson, Ill.; Mark A. Plummer; Carle C. Zimmerman, Jr., both of Littleton, Colo.; Henry J. Pietrzak, Texas City, Tex.; Wayne E. Luetzelschwab, Littleton, Colo.; Kent W. Robinson, Englewood, Colo.; Donald E. Schroeder, Jr., Littleton, Colo.

[73] Assignee: Marathon Oil Company, Findlay, Ohio

[22] Filed: Nov. 2, 1973

[21] Appl. No.: 412,062

[52] U.S. Cl............................ 260/505 S; 260/505 P
[51] Int. Cl.²........................................ C07C 143/24
[58] Field of Search .......... 260/505 S, 505 P, 505 C

[56] References Cited
UNITED STATES PATENTS

| 2,828,331 | 3/1958 | Marisic et al....................... | 260/505 |
| 3,346,505 | 10/1967 | Blakeway et al.................... | 260/505 |

FOREIGN PATENTS OR APPLICATIONS

| 682,714 | 2/1953 | United Kingdom................. | 260/505 |

*Primary Examiner*—James O. Thomas, Jr.
*Assistant Examiner*—A. Siegel
*Attorney, Agent, or Firm*—John R. Coleman, Jr.

[57] ABSTRACT

Petroleum sulfonates useful to impart micellar characteristics to mixtures of hydrocarbon and aqueous medium are obtained by reacting a hydrocarbon gas oil feedstock (average molecular weight 250–700; A/AP aliphatic to aromatic proton) ratio 5–50 moles/mole, 30–100% of the feedstock molecules contain aromatic portions and the A/AP ratio of the aromatic portion being about 3–20 moles/mole) with a solution of EDC (ethylene dichloride) containing 0.1–0.3 lb. liquid $SO_3$/lb EDC. The $SO_3$ concentration is about 0.1–0.3 lb. of $SO_3$/lb of gas oil feedstock. Reaction takes place in a back-mix tubular reactor wherein at least about 4 parts of reaction products are recycled per 1 part of reaction products withdrawn and wherein the gas oil feedstock plus recycled reaction products and the $SO_3$/EDC streams entering the reaction zone are in turbulent flow. Velocity ratio of the feedstock plus recycled reaction products stream to the $SO_3$/EDC stream is at least 4:1, respectively. The withdrawn reaction products are neutralized with an aqueous basic liquid, e.g. aqueous solution, $NH_4OH$ and thereafter the EDC is recovered from the neutralized reaction products to obtain unextracted sulfonate mix. The unextracted sulfonate mix is extracted with an aqueous alcohol solution to obtain a raffinate phase, an extract phase, and a brine phase; the extract phase is withdrawn and stripped of alcohol and water to obtain the desired petroleum sulfonate.

25 Claims, 9 Drawing Figures

PROCESS FOR THE PRODUCTION OF PETROLEUM SULFONATE

BACKGROUND OF THE INVENTION

1. Field of the Invention.

This invention relates to the manufacture of petroleum sulfonates especially useful to impart micellar characteristics to hydrocarbon and water mixtures. The sulfonatable feedstock is a gas oil having a particular molecular weight range, a particular A/AP ratio, etc. 3 is effected with liquid $SO_s$ diluted in EDC and the sulfonic acids are neutralized with preferably a monovalent cation-containing base.

2. Description of the Prior Art.

U.S. Pat. No. 3,254,714 to Gogarty et al teaches injection and displacement of a microemulsion made up with petroleum sulfonate, through an oil-bearing subterranean formation to recover crude oil therefrom. U.S. Pat. No. 3,497,006 to Jones et al teaches oil recovery processes using high water content, i.e. 55–$\pi$% water, oil-external micellar dispersions composed of petroleum sulfonate having an average molecular weight range of about 350–520. Jones, in U.S. Pat. No. 3,506,071 uses water-external micellar dispersions to recover crude oil. U.S. Pat. No. 3,302,713 to Ahearn et al floods with an aqueous solution containing a petroleum sulfonate having an average molecular weight of 450–500. Ahearn's sulfonates are obtained by sulfonating with gaseous $SO_3$ a hydrocarbon having a boiling point range of 700–1100°F.

U.S. Pat. No. 3,373,808 to Patton waterfloods with sulfonates obtained by sulfonating a hydrocarbon (having a boiling point range of 500°–1500°F.) with gaseous $SO_3$ or liquid $SO_3$ trimmer. The sulfonate hydrocarbons occurring in this boiling point range have an average molecular weight of about 250–700. Patton teaches that polysulfonation can be obtained by increasing the reaction temperature and the molar ratio of the sulfonating agent. In Example II, his hydrocarbon feedstock is first blended with equal volumes of 1,2-dichloroethane and then sulfonated with an inert vapor containing 8% gaseous $SO_3$—an equal molar amount of $SO_3$ is added per mole of sulfonatable hydrocarbon. The reaction mixture is then neutralized with an aqueous isopropanol solution containing sodium hydroxide, permitted to phase separate and the middle layer is recovered. The middle layer is evaporated of the dichloroethane and isopropanol to obtain the desired sulfonate product.

Patton in U.S. Pat. No. 3,373,808 teaches that only the molecular weight and API gravity of the feedstock need be specified. Applicants have found, however, that sulfonates from two different gas oils with nearly the same molecular weights and API gravities, e.g. Canadian and Michigan gas oils with molecular weights and API gravities at 60°F. of 438–439 and 25–26, respectively, impart considerably different micellar characteristics to hydrocarbon and water mixtures. Therefore, the A/AP ratio of the gas oil feedstock which Applicants teach is critical.

U.S. Pat. No. 2,168,315 to Blummer extracts mahogany sulfonates from a sulfonate mixture containing entrained oil and inorganic salts by contacting the mixture with an aqueous isopropyl alcohol mixture while maintaining the pH of the mixture at 3–9; a first liquid layer free from inorganic salts and containing organic solvent and mahogany sulfonates plus entrained oil is obtained and a second layer containing water and inorganic salts is formed.

U.S. Pat. No. 2,828,331 to Marisic et al teaches sulfonating petroleum oils at 10°–150°F, by injecting $SO_3$ into a hydrocarbon stream under turbulent flow. The $SO_3$ stream and the hydrocarbon stream can be diluted with ehtylene chloride if desired.

SUMMARY OF THE INVENTION.

Monovalent cation-containing petroleum sulfonates capable of imparting micellar characteristics to mixtures of water and hydrocarbon are obtained by sulfonating a hydrocarbon gas-oil feedstock having an average molecular weight of 250–700, an A/AP (aliphatic to aromatic proton ratio) of about 5–50 moles/mole, and having an aromatic content of at least about 30%, with liquid $SO_3$ diluted in EDC (ethylene dichloride). The amount of $SO_3$ introduced into the reaction is about 0.1–0.3 lb/lb of gas oil feedstock and the $SO_3$ concentration in the EDC is about 0.1–0.3 lb/lb, respectively. Sulfonation is carried out in a back-mix tubular reactor, the reactor having a pump to insure minimum velocity requirements and a heat exchanger to maintain the reaction product temperature at 100°–250°F. A major portion of the reaction products (EDC, sulfonic acids, resulting from the sulfonation of the gas oil, $SO_3$, $H_2SO_4$, and unreacted gas oil) is recycled while a portion is withdrawn to be neutralized. The $SO_3$/EDC stream is in turbulent flow when it contacts the gas-oil feedstock plus recycle reaction products which is also in turbulent flow--velocity ratio of the gas oil feedstock stream plus recycle reaction products stream to the $SO_3$/EDC stream is at least 4:1, respectively. The $SO_3$EDC stream enters at substantially right angles to the flow of the gas oil feedstock plus recycle reaction products and is introduced in such a manner that eddies of the recycled reaction products and the gas oil feedstock are prevented from getting into the nozzle or outlet of the $SO_3$/EDC stream; if such were permitted, a highly sulfonated "tarry" by-product would form. Also, the nozzle that introduces the $SO_3$/EDC stream should be located in such a manner to minimize the amount of SO $_3$ entering the boundary layer of the flowing streams adjacent to the reactor walls.

After the sulfonation reaction, a portion of the reaction products is withdrawn and neutralized with an aqueous basic solution containing a monovalent cation, e.g. $NH_4OH$ or $NaOH$, to obtain the neutralized reaction products. Thereafter, all or a substantial portion of the EDC and some water is stripped from the neutralized reaction products; the resulting unextracted sulfonate mix (neutralized reaction products substantially stripped of EDC and some water) is contacted with an aqueous alcohol solution which permits extraction of the desired petroleum sulfonates.

DESCRIPTION OF THE DRAWINGS

FIG. 2 illustrates the back-mix tubular reactor having a pump and heat exchanger within the closed loop reactor. Gas oil feedstock is fed into the main reaction stream and the recycled reaction products plus the "virgin" gas oil feedstock, its velocity designated as $V_1$, is then contacted with the $SO_3$/EDC stream, its velocity designated as $v_2$, note the $SO_3$/EDC stream enters at 90° angle to the recycled reaction products plus gas oil feedstock. The $SO_3$/EDC nozzle protects the $SO_3$/EDC stream from eddies of the recycled reaction products plus gas oil feedstock from getting into the nozzle and forming a highly sulfonated tar product. From the reaction zone, the reaction products enter the heat exchanger where the temperature of the reaction products is maintained at about 100° to about 250°F. Thereafter, a portion of the reaction products is withdrawn and transferred to the neutralization reactor. The velocity ratio ($V_1/V_2$) of the recycle reaction products plus gas oil feedstock to the velocity of the $SO_3$/EDC stream, both streams being in turbulent flow, is at least 4:1, respectively.

FIGS. 3a and 3b indicate the effect of the $SO_3$ treat (i.e. lb. of $SO_3$ per lb. of gas oil feedstock) on conversion of gas oil and $SO_3$ to sulfonate. Data for these curves were obtained in a back-mix tubular reactor wherein the $SO_3$ concentration in the EDC was 0.125 lb/lb, respectively, the velocity ratio of the recycled reaction products plus gas oil feedstock to the $SO_3$/EDC stream was 4:1, respectively; and about 10 parts of the reaction products were recycled per part of reaction products withdrawn. The velocity ratio ($V_1/v_2$) was about 4:1 and the reaction products temperature downstream of the reaction zone was maintained at 150°F. Gas oils having average molecular weights of about 417 to about 428 were sulfonated. FIG. 3a indicates the conversion of the gas oils to sulfonate based on $SO_3$ treat whereas FIG. 3b indicates the conversion of $SO_3$ to sulfonate based on the $SO_3$ treat. Based on economics of the process, these figures make it apparent that the desired $SO_3$ treat level is about 0.10–0.30 lb $SO_3$/lb. of the gas oil feedstock and more preferably about 0.10 to about 0.20. From FIG. 3b it is apparent that the conversion of $SO_3$ to sulfonate decreases as the $SO_3$ treat level increases; this means that a higher percentage of $SO_3$ is converted to by-products. Also, as the $SO_3$ treat level increases, more polysulfonation occurs which, in turn, decreases the equivalent weight of the petroleum sulfonate--a sulfonate equivalent weight below about 350 can adversely influence the ability of the petroleum sulfonate to impart micellar characteristics to hydrocarbon and aqueous medium mixtures.

FIGS. 4a and 4b illustrate the effect of the liquid $SO_3$ concentration in the EDC on the $SO_3$ and gas oil conversions to sulfonate in a back-mix tubular reactor. The gas oil feedstock has an average molecular weight of 409–419; the $SO_3$ treat level was 0.16 lb/lb feedstock, the velocity ratio of the recycle reaction products plus gas oil feedstock to the $SO_3$/EDC stream was greater than about 4:1, respectively; the ratio of recycled reaction products to reaction products withdrawn was 10 parts/part, respectively, to maintain a 4:1 velocity ratio and the reactor temperature was maintained at 150°F. As noted from these figures, at an $SO_3$/EDC ratio less than 0.1 lb $SO_3$/lb EDC, two phases exist, as such, the process will not effectively produce the desired sulfonate in the back-mix tubular reactor. Also, at concentrations greater than 0.30 lb. $SO_3$/lb. EDC, resulting sulfonates will not impart desired micellar characteristics to mixtures of hydrocarbon and aqueous medium. These figures indicate that as the $SO_3$/EDC ratio is increased, the conversion of gas oil and $SO_3$ to sulfonate decreases.

PREFERRED EMBODIMENTS OF INVENTION

The gas oil feedstocks are sulfonated with liquid $SO_3$ diluted in EDC. Concentration of $SO_3$ in the EDC and the $SO_3$ treat, based on the gas oil feedstock, is critical as is illustrated in the figures and explained later. The desired reaction of the $SO_3$ and the gas oil feedstock to produce sulfonic acids is illustrated by the formula (R is the feedstock, $n$ represents the degree of sulfonation, i.e. 1, 2, 3, etc.):

$$R + nSO_3 \rightarrow [R(SO_3H)_n]$$

The reaction products also contain unreacted gas oil and by-products such as sulfuric acid, sulfur dioxide, etc. Sulfonic acids in the reaction products are neutralized with an aqueous basic solution, preferably one containing a monovalent cation, e.g. an aqueous $NH_4OH$ or $NaOH$ solution, to obtain neutralized reaction products. Thereafter, the EDC is recovered from the neutralized reaction products and the EDC is dried and recirculated back to the sulfonation reactor. The resulting unextracted sulfonate mix is then contacted with an aqueous alcohol (preferably isopropanol) solution to form a raffinate phase, an extract phase, and a brine phase. The raffinate phase is separated and subjected to further processing to recover the unreacted gas oils and alcohol. The brine phase contains mostly water and salts, e.g. ammonium sulfate which can be recovered and used as a fertilizer. Alcohol can be recovered from the brine phase, if desired, by a simple stripping operation. The desired petroleum sulfonate product is in the extract phase which phase can be further processed to recover the alcohol.

Petroleum sulfonates obtained from this process have a particular HLB (hydrophil-lipophil balance) which indicates a particularly desired characteristic to impart micellar characteristics to mixtures of hydrocarbon and aqueous medium. These particular sulfonates are useful to obtain micellar dispersions which have utility in many fields of use, especially in the recovery of oil from subterranean reservoirs. Examples of specific uses of these petroleum sulfonates are taught in U.S. Pat. Nos. 3,254,714, 3,497,006, 3,506,071, etc.

Gas-Oil Feedstock

The hydrocarbon gas oil feedstock should have an average molecular weight of about 250 to about 700, preferably 300 to about 500 and more preferably 350 to about 450. The A/AP ratio of the feedstock, i.e. the number of aliphatic protons to the number of aromatic protons on the average molecule of the feedstock, is about 5 to about 50, preferably 10 to about 45 and more preferably 15 to about 40, respectively. The aromatic content of the feedstock should be at least about 30%, preferably 40 to about 80% and more preferably 40 to about 60% by weight. Also, the aromatic portion of the feedstock should have an A/AP ratio of about 3 to about 20 and preferably about 4 to about 18 moles per mole.

$SO_3$/EDC

The $SO_3$ is extremely reactive with the gas oil feedstock. It must be diluted with a solvent to promote a more even sulfonation reaction. EDC and like solvents are useful for this purpose. Without EDC, a highly sulfonated "char" is produced and plugging of the reactor is likely. The EDC acts as a viscosity control agent and thermal diluent for the reaction. Also, the EDC reduces side reactions, e.g. inhibits reaction of $SO_3$ to produce sulfuric acid and sulfur dioxide.

Figure 4A:
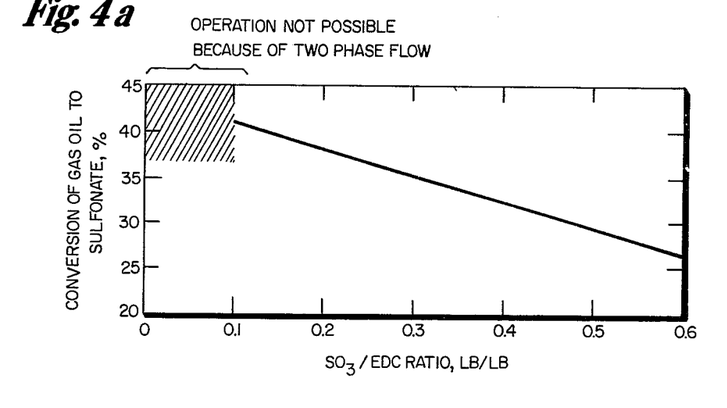
Figure 4B:
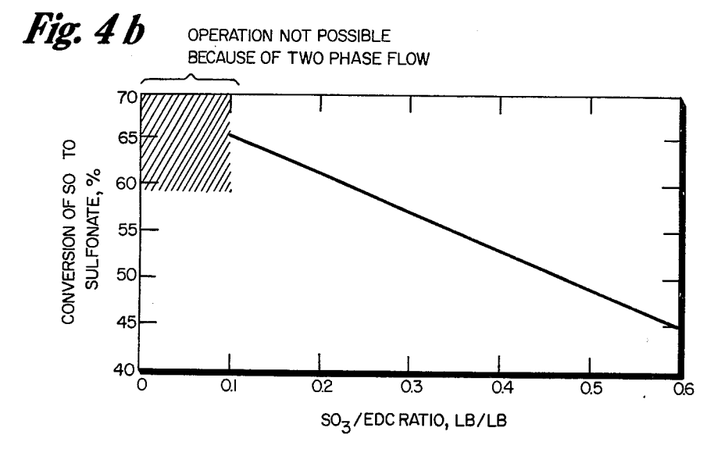
Figure 5:
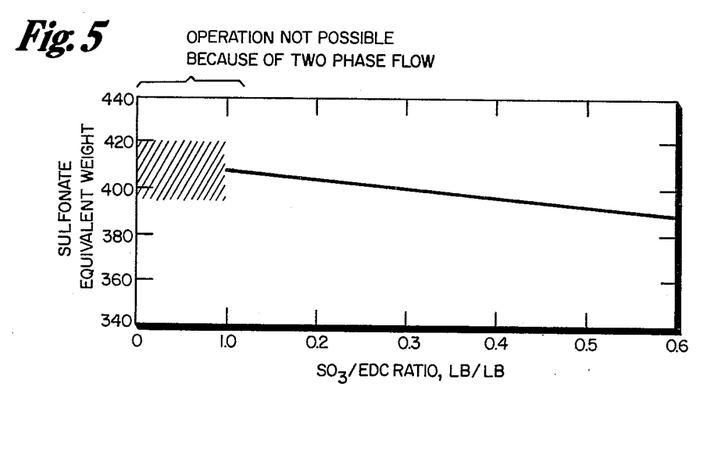
FIG. 5 indicates that as the $SO_3$/EDC ratio increases, the sulfonate equivalent weight decreases.

Concentration of the $SO_3$ in EDC is critical, i.e. it should be within the range of about 0.1 to about 0.3 lb. per lb. of EDC and preferably about 0.1 to about 0.2 lb. per lb. of EDC. At concentrations less than 0.1 lb $SO_3$ per lb of EDC, two phases exist which result in inefficient reaction of the $SO_3$ with the gas oil feedstock, see FIGS. 4a, 4b, and 5. As the concentration of $SO_3$ in EDC increases, the conversion of $SO_3$ and gas oil to sulfonic acid decreases, see FIGS. 4a and 4b. At concentrations greater than 0.3 lb of $SO_3$ per lb of EDC, the resulting petroleum sulfonate is not effective to impart desired micellar characteristics of mixtures of hydrocarbon and aqueous medium. Concentrations of about 0.125 lb. of $SO_3$ per lb. of EDC permits very efficient and economic operation with this invention.

The reaction of the gas oil with the $SO_3$ is extremely fast, on the order of 0.01–0.02 seconds.

Since $SO_3$ is reactive with the EDC, contact time between these two materials should be minimized. However, it is necessary that the $SO_3$ be thoroughly mixed with the EDC before contacting the gas oil. This is accomplished by introducing the $SO_3$ into turbulent flow of the EDC preferably at least 10 pipe diameters before the $SO_3$ comes in contact with the gas oil feedstock.

Figure 3A:
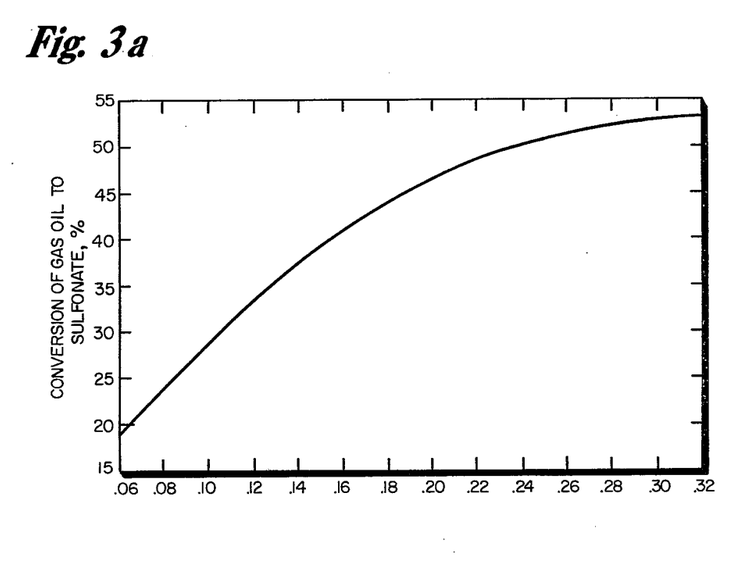
Figure 3B:
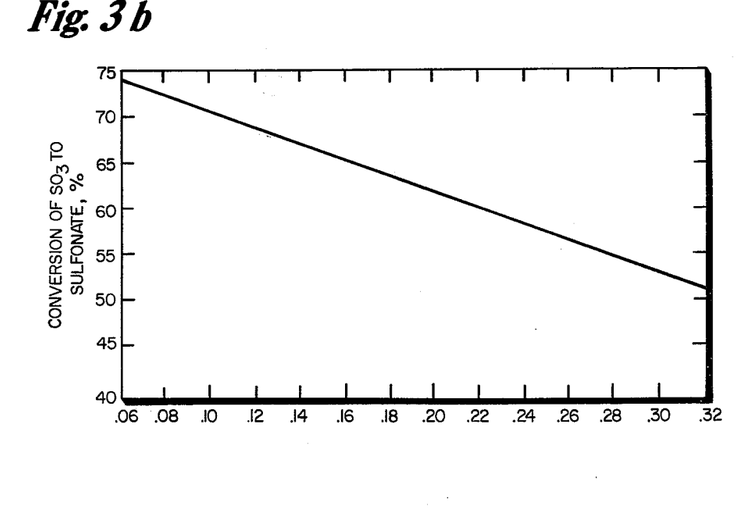

The $SO_3$ treat should be within the range of about 0.05 to about 0.3 and preferably about 0.10 to about 0.20, and more preferably about 0.12 to about 0.18 lb. $SO_3$ per lb. of gas oil feedstock. As is illustrated in FIGS. 3a and 3b, the conversions of gas oil and $SO_3$ to sulfonate are dependent upon the $SO_3$ treat level, e.g. as the $SO_3$ treat level increases, so does the conversion of gas oil to sulfonate — see FIG. 3a. However, the conversion of $SO_3$ to sulfonate decreases as the $SO_3$ treat level increases, see FIG. 3b. As the $SO_3$ treat level increases, so do the by-products, i.e. sulfuric acid, sulfur dioxide, etc. In addition, the quality of the sulfonate at high $SO_3$ treat levels, e.g. a charred, very viscous petroleum sulfonate, can be obtained. Thus, it is critical that the $SO_3$ treat level be within the range of the above parameters to obtain the desired sulfonate.

Reaction

Figure 2:
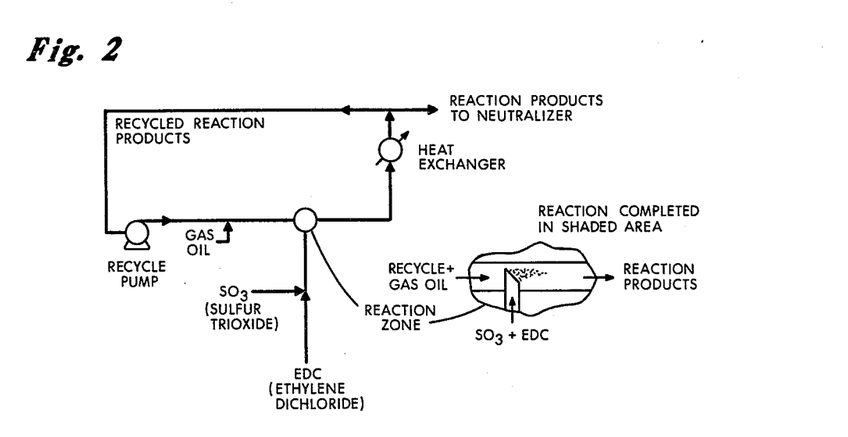

The gas oil feedstock and the $SO_3$ are reacted in a turbulent flow condition. The reactor is a back-mix tubular reactor having a pump and heat exchanger. Such a reactor is illustrated in FIG. 2 wherein recycled reaction products are admixed with gas oil feedstock and then contacted with the $SO_3$/EDC stream. The resulting reaction products enter a heat exchanger wherein the temperature is maintained preferably at about 100°F. to about 250°F. After the heat exchanger, a portion of the reaction products, e.g. about 4 to about 1 part and more preferably about 6 to about 1 part, is recycled per part of reaction product withdrawn to be neutralized. The recycled reaction products act as a thermal diluent and permit more efficient sulfonation of the gas oil feedstock.

Figure 6A:
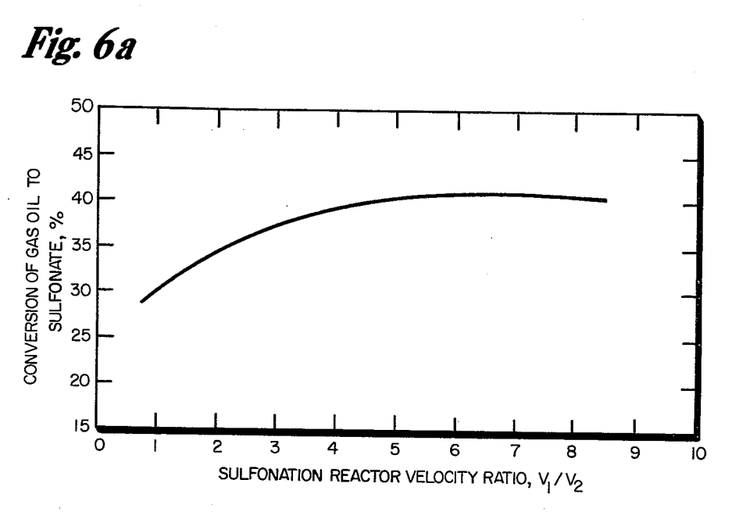
FIGS. 6a and 6b indicate the criticality of the sulfonation reaction zone, i.e. where the gas oil feedstock and recycle reaction products come in contact with the $SO_3$/EDC stream, the velocity ratio of $V_1$ to $V_2$ must be at least about 4:1, respectively. The gas oil feedstock plus recycled reaction products stream and the $SO_3$/EDC stream must be in turbulent flow.
Figure 6B:
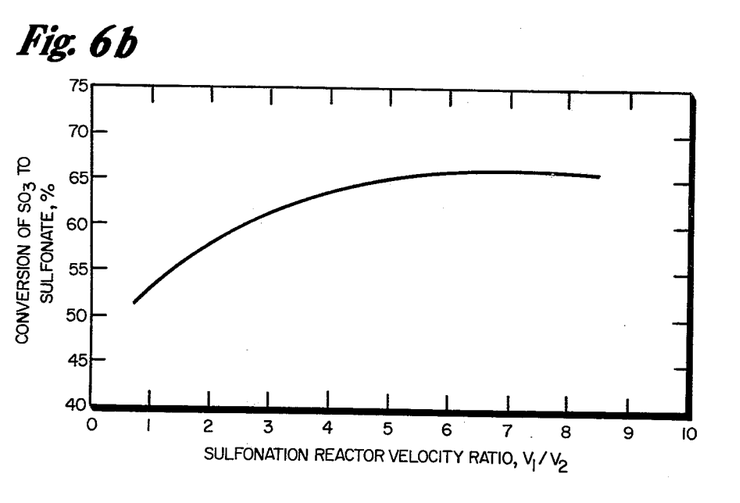

The velocity ratio of the recycled reaction products and the gas oil feedstock to the $SO_3$/EDC stream is critical, this velocity ratio must be at least greater than 4:1, and preferably 4.5:1, respectively, to obtain good conversions of $SO_3$ and gas oil — see FIGS. 6a and 6b. The amount of reaction products which are recycled can be varied to insure that the desired velocity ratio is maintained.

Preferably, the gas oil feedstock plus the recycled reaction products are contacted with the $SO_3$/EDC stream in a reaction zone in which the streams are impinged at substantially right angles, see FIG. 2.

The virgin gas oil feedstock can be introduced either upstream or downstream of the recycle pump, but should be introduced at a point which permits efficient mixing of the gas oil in the recycled reaction products before coming in contact with the $SO_3$/EDC stream.

Preferably, the $SO_3$/EDC stream is introduced into the gas oil feedstock plus recycled reaction products stream through a nozzle which is shaped to prevent eddies of the recycled reaction products and gas oil stream from getting into the nozzle and forming a highly sulfonated "tar" deposit on contact with the $SO_3$. Also, the open face of the $SO_3$/EDC nozzle should be located to minimize the amount of $SO_3$ entering the boundary layer of the reactor wall. This can be accomplished by keeping the terminal end of the nozzle about 20% of the diameter of the reactor tube from the reactor wall of the tubular reactor, and the bottom part of the open nozzle at least about 20% of the diameter of the reactor tube or greater from the reactor wall.

Temperature of the reaction products immediately past the reaction zone should be maintained between about 100° and about 250°F. Temperatures greater than 250°F. can result in charred products and such are undesirable for this invention. A heat exchanger located downstream of the juncture of the gas oil feedstock plus recycled reaction products stream and the $SO_3$/EDC stream is sufficient to maintain this temperature range.

The reactor must be operated under pressure sufficient to prevent the EDC and any by-products, e.g. $SO_2$, from vaporizing. If permitted to vaporize, this can cause pump cavitation and, as a result, poor product quality.

A centrifugal pump or like pump is sufficient for the recycle pump.

The velocity of the gas oil feedstock plus recycled reaction products to the velocity of the incoming $SO_3$/EDC stream is critical as evidenced in FIGS. 6a and 6b. At low velocity ratios, poor product quality is realized as well as poor conversions of gas oil feedstock and $SO_3$ to sulfonate. However, at velocity ratios greater than 6, little improvement is realized as is evidenced from these figures.

Recycle Ratio

The minimum amount of recycled reaction products to the reaction products withdrawn for neutralization is dictated by the acceptable rise in temperature upon sulfonation. A recycle ratio of 2:1 is sufficient provided the recycle stream is sufficiently cooled. Preferably at least 6 parts is recycled per part withdrawn to insure the critical aforementioned velocity ratio.

Neutralization of the reaction products

As mentioned previously, the reaction products are removed from the sulfonation reactor to be neutralized. The reaction products contain sulfonic acids, by-product sulfuric acid and $SO_2$, and unreacted gas oil, EDC, etc. The reaction products are fed to a neutralization zone wherein the sulfonic acids are neutralized with an aqueous basic liquid, preferably an aqueous ammonium hydroxide or sodium hydroxide solution. The aqueous ammonium hydroxide solution can be obtained by injecting ammonia into water. Preferably, the sulfonic acids are neutralized with the aqueous ammonium hydroxide solution in a back-mix tubular reactor similar to that used in the sulfonation reaction zone.

The sulfonic acids, sulfuric acid, $SO_2$, etc. are neutralized with the aqueous basic liquid. The neutralized reaction products contain, e.g. when neutralized with an aqueous ammonium hydroxide solution, ammonium petroleum sulfonate, ammonium sulfate, ammonium sulfite, EDC, etc. and unreacted gas oils.

In the neutralization reactor, two types of chemical reactions are involved: first, neutralization reactions of ammonium hydroxide with sulfonic acids, sulfuric acids, and sulfur dioxide; and secondly, a slow reaction of ammonia with EDC. It is preferred that only a negligible amount of EDC reacts with the ammonia, i.e. less than about 0.02 weight percent — short residence times, e.g. less than one minute, tend to reduce this reaction.

Within the neutralization reaction zone, the sulfonic acids mix with the basic liquid neutralizer to form, e.g. ammonium petroleum sulfonate. The neutralized reaction products facilitate solubilization of the organic salts in the aqueous basic liquid.

The desired pH of the neutralized reaction products is about 5 to about 9 and preferably about 6.0 to about 6.5. Also, it is desired that the temperature of the neutralization reaction be maintained below about 175°F.

Desirably the neutralization reactor is maintained under back pressure sufficient to keep the ammonia as a liquid after it is introduced into the water.

Ammonium hydroxide and sodium hydroxide are especially useful as neutralizers for this process. Other basic liquids such as potassium hydroxide, etc. are also useful.

EDC recovery

After the reaction products are neutralized, the neutralized reaction products are heated to vaporize the EDC. The EDC is recovered and is preferably dried and then recycled back to the sulfonation reactor as a solvent. Steam can be injected to facilitate stripping the EDC from the neutralized reaction products at a temperature within the range of about 220° to about 250° and more preferably about 235° to about 245°F. This temperature limitation is necessary to prevent decomposition of the petroleum sulfonate. Stripping of the EDC from the neutralized reaction products can be effected in a packed tower, etc. Drying the EDC before recycling is preferred since any water present will react with $SO_3$ to form $H_2SO_4$.

Extraction

After the EDC is stripped from the neutralized reaction products, the resulting unextracted sulfonate mix is contacted with preferably an aqueous alcohol solution to permit extraction of the petroleum sulfonate. Examples of useful alcohols include those containing from 1 to about 5 carbon atoms. Semi-polar organic compounds, such as benzene, are useful as the extraction solvent. Preferably, the extraction solvent is an aqueous isopropanol solution containing about 50 to about 80%, preferably 55-75% and more preferably 60-70% by weight isopropanol. Other alcohols or like organic compounds are useful with the invention.

The oil and salt content of the final petroleum sulfonate product is controlled by both the solvent to unextracted sulfonate mix ratio and the solvent composition. That is, about 0.8-2.0 lbs., preferably 1.0-1.8 lbs. and more preferably 1.1-1.5 lbs. of aqueous alcohol solution is mixed with each lb. of the unextracted sulfonate mix; the unextracted sulfonate mix can contain water, e.g. about 15%.

The isopropyl alcohol solution on contact with the unextracted sulfonate mix forms at least three phases, i.e. a *raffinate* phase which consists mostly of unreacted oil, an *extract* phase which contains the petroleum sulfonate product, and a *brine* phase which contains salts and water.

Formation of the three phases during the extraction step can be controlled by the choice of the ratio of solvent to unextracted sulfonate mix and solvent composition. It is important to maintain a sufficiently dense extract phase to prevent inversion of the extract and raffinate phases. The optimum density difference between the raffinate and extract phase is preferably about 5 API degrees and more preferably about 10 API degrees, e.g. if the raffinate density is about 30 API degrees, the solvent composition should be adjusted to maintain an extract density in the range of about 20 to about 25 API degrees.

The raffinate phase is subjected to processing conditions to recover the alcohol and water from the unreacted gas oil. The unreacted gas oil is recovered and is useful for further refining, e.g. as feedstock to a catalytic cracker.

The brine phase can be disposed of or can be further processed to recover the ammonium sulfate which is useful as a fertilizer, etc.

The extract phase is fed to a stripper wherein the alcohol and water is recovered from the petroleum sulfonate. The recovered petroleum sulfonate is the desired product of this process.

Figure 1:
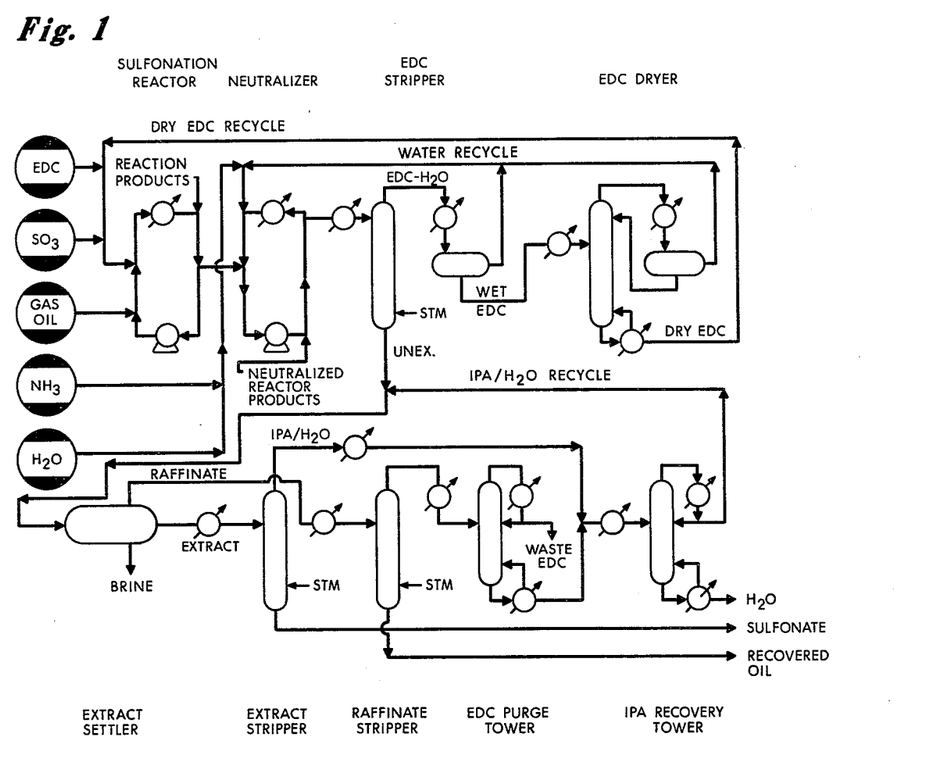
FIG. 1 illustrates the sulfonation process flow diagram wherein the gas oil feedstock is sulfonated with liquid $SO_3$ diluted in EDC, the resulting reaction products are neutralized with $NH_4OH$ (resulting from adding $NH_3$ to water) and the EDC and some water (referenced "$H_2O$") is recovered. STM, i.e. steam, can be used to strip the EDC. The EDC is dried and recycled back to the sulfonation reactor. Unextracted sulfonate mix (referenced "UNEX") is then contacted with IPA (isopropanol) water mixture and permitted to phase separate into a raffinate phase, an extract phase, and a brine phase in the extract settler. The raffinate phase is subjected to further processing to recover IPA and unreacted gas oil (referenced "recovered oil"), the brine phase is disposed of or processed further to recover ammonium sulfate, and the extract phase is stripped of the IPA and some water and the petroleum sulfonate recovered as the desired product. The recovered IPA is recycled to contact the unextracted sulfonate mix. Additional EDC is added to the $SO_3$/EDC stream as make-up.

The recovered aqueous alcohol solution can be further processed and then recycled back to the sulfonation process flow diagram as illustrated in FIG. 1.

The desired petroleum sulfonate product has an average equivalent weight within the range of about 350 to about 525, preferably about 375 to about 475 and more preferably about 390 to about 445. This average equivalent weight range is a quality control parameter and is directly related to the capability of the petroleum sulfonate to impart desired micellar characteristics to mixtures of hydrocarbon and aqueous medium. Equivalent weight is defined as the sulfonate molecular weight divided by the average number of sulfonate groups per molecule. It indicates the relative amount of monosulfonation and polysulfonation, i.e. the equivalent weight becomes lower as the polysulfonation increases.

EXAMPLES

The following examples are presented to specifically illustrate working embodiments of the invention. Unless otherwise specified, all percents are based on volume.

EXAMPLE I

A heavy vacuum gas oil feedstock having an average molecular weight of about 419, an A/AP ratio of 22.1 moles/mole, and wherein about 55% of the hydrocarbon molecules within the gas oil contain an aromatic nucleus and wherein the aromatic portion exhibits an A/AP ratio of 9.5 moles/mole, is sulfonated in a back-mix tubular reactor with liquid $SO_3$ dissolved in EDC. The $SO_3$ concentration in the EDC is 0.125 lb/lb, respectively. Velocity ratio of the gas oil feedstock plus recycle reaction products stream to the incoming liquid $SO_3$EDC stream is greater than 4:1, respectively. Ten parts of reaction products are recycled per part of reaction product withdrawn from the reactor. Temperature downstream of the reaction zone is maintained at 150°F. The $SO_3$ treat varies from about 0.06 to about 0.32 lb. $SO_3$/lb. gas oil feedstock — specific runs are illustrated in FIGS. 3a and 3b. The circles within these figures represent the above gas oil. The trangular data points having the base of the triangle on the top side, represent a gas oil feedstock having an average molecular weight of 424, an A/AP ratio of 21 moles/mole. The other trangular data points represent a gas oil having an average molecular weight of 428 and an A/AP ratio of 22.3 moles/mole. The A/AP ratios of the aromatic portions of the above three feedstocks is about 9–10 moles/mole. FIG. 3a illustrates that the conversion of the gas oil to sulfonate depends upon the $SO_3$ treat. FIG. 3b indicates the conversion of $SO_3$ to sulfonate is dependent upon the $SO_3$ treat.

The withdrawn reaction products are neutralized to a pH of 6.3–6.5 by contacting the acids with an aqueous solution of $NH_4OH$ at a temperature of about 150°–165°F. The aqueous $NH_4OH$ solution is obtained by injecting $NH_3$ into water. Thereafter, the EDC is stripped from the neutralized reaction products at a temperature of about 235°–245°F. in a packed tower. Steam is injected into the bottom of the stripping tower at the rate of about 0.15 parts of steam (saturated steam at 20–40 psia) per part of unextracted sulfonate mix (neutralized reaction products substantially free of EDC). The EDC is recovered and dried by conventional methods and then recycled back to the sulfonation reactor; fresh EDC is added as make-up.

The unextracted sulfonate mix is then admixed with about 0.8 to about 1.7 lbs. of IPA (isopropyl alcohol/water solution (the concentration and amount of the IPA/water solvent depends upon the concentration of water within the unextracted sulfonate mix and also the $SO_3$ treat). The resulting mixture is passed to an extract settler operated at about 130°–200°F. and more preferably 150°–170°F. Three phases are formed, a raffinate phase, an extract phase, and a brine phase.

The raffinate phase (containing mostly IPA and unreacted oil) is separated and passed to a stripper where the IPA is stripped from the unreacted oil. The stripping tower is operated at about 235°–245°F. Steam injected into the bottom of the stripper at a rate of about 0.05–0.75 lbs. of steam (saturated at 20–40 psia) per lb. of recovered oil (unreacted gas oil). The recovered IPA is further refined and then recycled to be admixed with the unextracted sulfonate mix.

The extract phase is stripped of the IPA and a majority of the water, this accomplished by passing the extract phase through a stripper tower run at about 235°–245°F.; steam can also be injected in the bottom of the tower to facilitate stripping of the IPA. The sulfonate is recovered at the bottom of the stripper as the desired product of this invention.

The brine phase can be disposed of or it can be further processed to recover the ammonium sulfate and alcohol it contains.

EXAMPLE II

The above procedure is repeated for two different heavy vacuum gas oil feedstocks, one gas oil having an average molecular weight of about 450, A/AP ratio of about 41 moles/mole, about 35% of the gas oil molecules have aromatic portions, and the A/AP ratio of the aromatic portion is about 10.8 moles/mole. The other gas oil has an average molecular weight of about 443, an A/AP ratio of about 33 moles/mole, about 37% of the molecules within the gas oil contain an aromatic portion, and an A/AP ratio of the aromatic portion is about 10.7 moles/mole.

The reaction products are passed to a back-mix tubular reactor containing a pump in line with a heat exchanger wherein the reaction products come in contact and are neutralized (to a pH of 6.3–6.5) with an aqueous ammonium hydroxide solution. The temperature downstream of the heat exchanger is maintained at 160°F. About 1 part of the neutralized reaction products is withdrawn per 2.5 parts of neutralized reaction products recycled.

The neutralized reaction products are then heated to 240°F. and passed to a stripper tower operated at about 16 psia wherein the EDC is stripped or removed from the unextracted sulfonate mix. Steam (30 psia) is injected into the bottom of the stripper at a rate of 0.15 lbs. of steam per lb. of unreacted sulfonate mix to facilitate removal of the EDC.

The EDC is recovered, further processed, dried, and then recycled back to the sulfonation reactor. The unextracted sulfonate mix (neutralized reaction products substantially free of EDC) is removed from the bottom of the stripper.

The unextracted sulfonate mix is then admixed with about 1.3 lbs. of an aqueous IPA solution (about 64% by weight IPA) per lb. of unextracted sulfonate mix. The resulting mixture is passed to an extract settler operated at about 160°F. wherein a raffinate phase, an extract phase, and a brine phase occurs. The raffinate phase is recovered and passed through a stripper operated at about 240°F. wherein the IPA is removed from unreacted gas oil. Steam is injected into the bottom of the stripper to facilitate stripping of the IPA, about 0.06 lbs. of 30 psia steam (saturated) is injected per lb. of unreacted gas oil. The IPA is further processed to remove the water and is then recycled to become admixed with the unextracted sulfonate mix.

The extract phase is passed to a stripper wherein the IPA and water are removed at a temperature of about 240°F. Steam (saturated at 30 psia) is injected into the bottom of the stripper at a rate of about 0.15 lbs. per lb. of recovered petroleum sulfonate product. The recovered IPA is further processed to remove the water and then is recycled to be admixed with the unextracted sulfonate mix. The recovered ammonium petroleum sulfonate is the desired product. It is used to impart micellar characteristics to mixtures of hydrocarbon and aqueous medium.

It is not intended that the examples limit the invention in any way. Rather, all equivalents obvious to those skilled in the art are intended to be incorporated within the scope of the invention as defined within the specification and appended claims.

What is claimed is:

1. A process for producing monovalent cation-containing petroleum sulfonates which are capable of forming a micellar dispersion when admixed with mixtures of hydrocarbon and aqueous medium, the process comprising reacting in a back-mix tubular reactor comprised of a pump, a reaction zone and heat exchanger:
   1. a hydrocarbon gas oil feedstock having an average molecular weight of about 250 to about 700 and an aliphatic to aromatic proton ratio of about 5 to about 50 moles per mole, and wherein at least about 30% of the feedstock molecules contain an aromatic nucleus, the aliphatic to aromatic proton ratio of the feedstock molecules containing the aromatic nucleus being about 3 to about 20 moles per mole,
   2. with an ethylene dichloride (EDC) solution containing about 0.1 to about 0.3 part of liquid $SO_3$ per part of the EDC and wherein the weight ratio of the $SO_3$ to the gas oil feedstock is about 0.05 to about 0.3 part of $SO_3$ per part of gas oil feedstock, and wherein the hydrocarbon gas oil feedstock plus recycled reaction products stream is under turbulent flow and the $SO_3$/EDC stream is under turbulent flow, but wherein the velocity ratio of the hydrocarbon gas oil feedstock plus recycled reaction products stream to the $SO_3$/EDC stream is at least 4:1, respectively,
   3. withdrawing about 1 part of the reaction products resulting from reaction of 1 and 2 for about 1 to about 6 parts of the reaction products recycled in the reactor, and neutralizing this portion of the reaction products to a pH of about 5 to about 9 with an aqueous basic solution containing a monovalent cation,
   4. removing substantially all of the EDC from the neutralized reaction products to obtain an unextracted sulfonate mix,
   5. contacting the unextracted sulfonate mix with sufficient amounts of an aqueous alcohol solution containing an alcohol which has sufficient solubility in the mixture to cause the resulting mixture to settle into at least a raffinate phase, an extract phase, and a brine phase.
   6. separating the raffinate phase, the raffinate phase containing mostly unreacted gas oil, alcohol and water,
   7. separating the brine phase, and
   8. separating the extract phase, the extract phase containing alcohol, water, and the petroleum sulfonate product, and removing a major portion of the alcohol and water from the extract phase to obtain the desired monovalent-containing petroleum sulfonates.

2. The process of claim 1 wherein the average molecular weight of the feedstock is about 300 to about 500.

3. The process of claim 1 wherein the average molecular weight of the feedstock is within the range of about 350 to about 450.

4. The process of claim 1 wherein the average aliphatic to aromatic proton ratio of the gas oil feedstock is about 10 to about 45 moles per mole.

5. The process of claim 1 wherein the average aliphatic to aromatic proton ratio of the gas oil feedstock is about 15 to about 40 moles per mole.

6. The process of claim 1 wherein the average aliphatic to aromatic proton ratio of the aromatic portion of the feedstock is about 4 to about 18 moles per mole.

7. The process of claim 1 wherein about 40 to about 80% of the gas oil feedstock molecules contain an aromatic nucleus.

8. The process of claim 1 wherein the $SO_3$ concentration in the EDC within step (2) is about 0.10 to about 0.20 part $SO_3$/part of EDC by weight.

9. The process of claim 1 wherein the weight ratio of $SO_3$ to the gas oil feedstock within step (3) is about 0.1 to about 0.2 part of $SO_3$/part of the feedstock by weight.

10. The process of claim 1 wherein the temperature of the reaction products exiting from the heat exchanger is within the range of about 100° to about 250°F. after reaction of (1) and (2).

11. The process of claim 1 wherein substantially all of the EDC is recovered from the neutralized reaction products.

12. The process of claim 1 wherein the velocity ratio of the gas oil feedstock plus recycled reaction products to the $SO_3$/EDC stream is at least 4.5:1, respectively.

13. The process of claim 1 wherein the aqueous alcohol solution of (5) contains about 50 to about 80% by weight of an alcohol containing about 1 to about 5 carbon atoms.

14. The process of claim 1 wherein the aqueous alcohol solution is an aqueous solution containing about 50 to about 80% by weight of isopropanol.

15. The process of claim 1 wherein the unextracted sulfonation mix is contacted with about 0.8 to about 2 parts of an aqueous isopropanol solution containing about 50 to about 80% by weight of isopropanol per part of the unextracted sulfonation mix.

16. A process for producing ammonium petroleum sulfonates having an average equivalent weight of about 375 to about 475 and which are capable of forming a micellar dispersion when admixed with mixtures of hydrocarbon and aqueous medium, the process comprising reacting in a back-mix tubular reactor comprised of a pump, a reaction zone and a heat exchanger:
   1. a hydrocarbon gas oil feedstock having an average molecular weight of about 300 to about 500, an aliphatic to aromatic proton ratio of about 10 to about 45 moles per mole, and wherein at least about 40 to about 80% of the gas oil feedstock molecules contain an aromatic nucleus, the aliphatic to aromatic proton ratio of the feedstock molecules containing the aromatic nucleus being about 4 to about 18 moles per mole,
   2. with an ethylene dichloride (EDC) solution containing about 0.1 to about 0.3 part of liquid $SO_3$ per part of the EDC and wherein the weight ratio of the $SO_3$ to the gas oil feedstock is about 0.1 to about 0.3 part of $SO_3$ per part of gas oil feedstock, and wherein the hydrocarbon gas oil feedstock plus recycled reaction products stream is under turbulent flow and the $SO_3$/EDC stream is under turbulent flow, but wherein the velocity ratio of the hydrocarbon gas oil feedstock plus recycled reaction products stream to thte $SO_3$/EDC stream is at least 4:1, respectively, the reaction products enter the heat exchanger where the temperature of the reaction products is maintained at about 100°F. to about 250°F., 3. withdrawing about 1 part of the reaction products resulting from reaction of (1) and (2) for about 1 to about 6 parts of the reaction products recycled in the reactor and neutralizing this portion of the reaction products with an aqueous ammonium hydroxide solution to a pH of about 5 to about 9,
4. removing substantially all of the EDC from the neutralized reaction products to obtain the unextracted sulfonate mix,
5. contacting the unextracted sulfonate mixture with about 0.8 to about 2 parts of an aqueous isopropanol solution containing about 50 to about 80% by weight of isopropanol per part of the unextracted sulfonation mix,
6. permitting the resulting mixture of (5) to phase separate into a raffinate phase, an extract phase, and a brine phase,
7. separating the raffinate phase which contains mostly unreacted gas oil, isopropanol, and water,
8. separating the brine phase, and
9. separating the extract phase and removing at least a portion of any alcohol and water present to obtain the desired ammonium petroleum sulfonate.

17. The process of claim 16 wherein the average molecular weight of the gas oil feedstock is within the range of about 350 to about 450.
18. The process of claim 16 wherein the aqueous isopropanol solution contains about 60 to about 70% by weight of isopropanol.
19. The process of claim 16 wherein the $SO_3$ concentration in the EDC within step (2) is about 0.1 to about 0.2 part of $SO_3$/part of EDC.
20. The process of claim 16 wherein the weight ratio of $SO_3$ to the gas oil feedstock within Step (2) is about 0.1 to about 0.2 part of $SO_3$/part of gas oil feedstock.
21. The process of claim 16 wherein the velocity ratio of the gas oil feedstock plus recycled reaction products stream to the $SO_3$/EDC stream is at least 4.5:1, respectively.
22. The process of claim 16 wherein substantially all of the isopropanol is separated from the raffinate phase and is recycled to step (5).
23. The process of claim 16 wherein the brine phase is comprised of ammonium sulfate and isopropanol and the ammonium sulfate and isopropanol are separated from the brine phase.
24. The process of claim 23 wherein the separated isopropanol is recycled to step (5).
25. The process of claim 16 wherein substantially all of the water is removed from the EDC recovered in Step (4) and at least a portion of the resulting EDC is recycled to the sulfonation reactor.

* * * * *

UNITED STATES PATENT OFFICE
CERTIFICATE OF CORRECTION

Patent No. 3,956,372                Dated May 11, 1976

Inventor(s) COLEMAN, JR. et al

It is certified that error appears in the above-identified patent and that said Letters Patent are hereby corrected as shown below:

Column 1, line 12    Delete "3" and insert --Sulfonation--

Column 1, line 21    Delete "$\pi$" and insert --90--

Column 13, line 9    Delete "thte" and insert --the--

Signed and Sealed this

Fifteenth Day of May 1979

[SEAL]

Attest:

RUTH C. MASON
*Attesting Officer*

DONALD W. BANNER
*Commissioner of Patents and Trademarks*